United States Patent
Pandya et al.

(10) Patent No.: US 11,963,688 B2
(45) Date of Patent: Apr. 23, 2024

(54) DEVICE ADAPTED FOR LATERAL ENGAGEMENT OF AN ELONGATED MEMBER

(71) Applicant: PanOrthopaedics, Inc., Atlanta, GA (US)

(72) Inventors: Rajiv D. Pandya, Atlanta, GA (US); Randall Allard, Golden, CO (US)

(73) Assignee: PANORTHOPAEDICS, INC., Atlanta, GA (US)

( * ) Notice: Subject to any disclaimer, the term of this patent is extended or adjusted under 35 U.S.C. 154(b) by 237 days.

(21) Appl. No.: 17/531,727

(22) Filed: Nov. 20, 2021

(65) Prior Publication Data
US 2023/0157707 A1    May 25, 2023

(51) Int. Cl.
*A61B 17/16*      (2006.01)
*A61B 17/17*      (2006.01)

(52) U.S. Cl.
CPC .......... *A61B 17/17* (2013.01); *A61B 17/1615* (2013.01); *A61B 17/1637* (2013.01); *A61B 17/1757* (2013.01); *A61B 17/1764* (2013.01); *A61B 17/1778* (2016.11)

(58) Field of Classification Search
CPC .............................. A61B 17/1637; A61B 17/17
See application file for complete search history.

(56) References Cited

U.S. PATENT DOCUMENTS

| | | | |
|---|---|---|---|
| 852,394 | A | 4/1907 | Moses |
| 4,257,411 | A | 3/1981 | Cho |
| 4,672,957 | A | 6/1987 | Hourahane |
| 4,722,331 | A | 2/1988 | Fox |
| 4,739,751 | A | 4/1988 | Sapega et al. |

(Continued)

FOREIGN PATENT DOCUMENTS

| | | |
|---|---|---|
| GB | 2230453 | 10/1990 |
| WO | 2009107121 | 9/2009 |

OTHER PUBLICATIONS

Rotator Cuff Tears and Treatment Options, Article 2007, pp. 1-9 American Academy of Orthopaedic Surgeons, Rosemont IL, Rotator Cuff Tear, 2008, pp. 1-3 ehealth MD.

*Primary Examiner* — Christian A Sevilla
(74) *Attorney, Agent, or Firm* — David O. Simmons; IVC Patent Agency

(57) ABSTRACT

A device for accessing extra articular lesions or abnormalities or intra osseous lesions or abnormalities or bone marrow lesions using intra articular localization has a guide, a locating arm, a set of attachment assemblies and a tubular sleeve. The device comprises a device body and an attachment assembly mounted on the device body. The attachment assembly includes a main body and at least one closure body. The main body has an elongated recess therein. The elongated recess is configured for receiving an elongated member therein along an entire length thereof. The at least one closure body is rotatably mounted on the main body. The elongated member may be positioned within the elongated recess via lateral movement when the at least one closure body is in a first rotational position relative to the main body. The elongated member may be retained within the elongated recess when the at least one closure body is moved away from the first rotational position toward a second rotational position relative to the main body.

15 Claims, 4 Drawing Sheets

(56) References Cited

U.S. PATENT DOCUMENTS

| | | | |
|---|---|---|---|
| 4,781,182 | A | 11/1988 | Purnell et al. |
| 4,920,958 | A | 5/1990 | Walt et al. |
| 5,112,337 | A | 5/1992 | Paulos et al. |
| 5,163,940 | A * | 11/1992 | Bourque ............ A61B 17/1764 606/88 |
| 5,330,468 | A | 7/1994 | Burkhart |
| 5,556,428 | A | 9/1996 | Shah |
| 5,562,669 | A | 10/1996 | Mcguire |
| 5,669,917 | A | 9/1997 | Sauer et al. |
| 5,671,695 | A | 9/1997 | Schroeder |
| 5,681,333 | A | 10/1997 | Burkhart et al. |
| 5,766,179 | A | 9/1998 | Faccioli et al. |
| 5,895,425 | A | 4/1999 | Grafton et al. |
| 6,120,511 | A | 9/2000 | Chan |
| 6,132,433 | A | 10/2000 | Whelan |
| 6,306,138 | B1 | 10/2001 | Clark et al. |
| 6,325,804 | B1 | 12/2001 | Wenstrom et al. |
| 6,517,546 | B2 | 2/2003 | Whittaker et al. |
| 6,537,319 | B2 | 3/2003 | Whelan |
| 6,610,064 | B1 | 8/2003 | Goble et al. |
| 6,623,524 | B2 | 9/2003 | Schmieding |
| 6,716,217 | B2 | 4/2004 | Mckeman et al. |
| 6,926,720 | B2 | 8/2005 | Casetnada |
| 7,025,786 | B2 | 4/2006 | Goble et al. |
| 7,032,599 | B2 | 4/2006 | May et al. |
| 7,056,340 | B2 | 6/2006 | McKeman et al. |
| 7,175,632 | B2 | 2/2007 | Singhatat et al. |
| 7,201,756 | B2 | 4/2007 | Ross |
| 7,270,666 | B2 | 9/2007 | Lomardo et al. |
| 7,338,492 | B2 | 3/2008 | Singhatat et al. |
| 7,458,975 | B2 | 12/2008 | May et al. |
| 7,491,206 | B2 | 2/2009 | Whittaker et al. |
| 7,569,059 | B2 | 8/2009 | Cerundolo |
| 7,594,922 | B1 | 9/2009 | Goble et al. |
| 7,594,930 | B2 | 9/2009 | Warlick et al. |
| 7,674,290 | B2 | 3/2010 | McKeman et al. |
| 7,678,138 | B2 | 3/2010 | Fitts et al. |
| 7,713,300 | B2 | 5/2010 | Meridew et al. |
| 7,766,964 | B2 | 8/2010 | Stone et al. |
| 7,955,341 | B2 | 6/2011 | Cerundolo |
| 7,998,203 | B2 | 8/2011 | Blum |
| 8,088,128 | B2 | 1/2012 | May et al. |
| 8,221,454 | B2 | 7/2012 | Schaffhausen |
| 8,251,998 | B2 | 8/2012 | Hoeppner et al. |
| 8,292,921 | B2 | 10/2012 | Stone et al. |
| 8,323,291 | B2 | 12/2012 | Dienst et al. |
| 8,382,835 | B2 | 2/2013 | Meridew et al. |
| 8,435,292 | B2 | 5/2013 | Whittaker |
| 8,500,740 | B2 | 8/2013 | Bojarski et al. |
| 8,512,405 | B2 | 8/2013 | Baird |
| 8,551,123 | B2 | 10/2013 | Pandya |
| 8,579,974 | B2 | 11/2013 | Pandya |
| 8,617,166 | B2 | 12/2013 | Hanson et al. |
| 8,617,176 | B2 | 12/2013 | Lizardi et al. |
| 8,821,504 | B2 | 9/2014 | Sharkey et al. |
| 8,864,768 | B2 | 10/2014 | Hanson et al. |
| 8,906,032 | B2 | 12/2014 | Hansen et al. |
| 8,951,261 | B2 | 2/2015 | Sharkey et al. |
| 9,033,987 | B2 | 5/2015 | Hanson et al. |
| 9,119,721 | B2 | 9/2015 | Sharkey et al. |
| 9,138,187 | B2 | 9/2015 | Sharkey |
| 9,259,257 | B2 | 2/2016 | Bagga et al. |
| 9,271,835 | B2 | 5/2016 | Bagga et al. |
| 9,351,746 | B2 | 5/2016 | Hanson et al. |
| 9,351,835 | B2 | 5/2016 | Sharkey et al. |
| 9,386,996 | B2 | 7/2016 | Hanson et al. |
| 2001/0053934 | A1 | 12/2001 | Schmieding |
| 2003/0065391 | A1 | 4/2003 | Re et al. |
| 2003/0167090 | A1 | 9/2003 | Chervitz et al. |
| 2003/0176919 | A1 | 9/2003 | Schmieding |
| 2004/0059415 | A1 | 3/2004 | Schmieding |
| 2004/0087978 | A1 | 5/2004 | Velez et al. |
| 2004/0194789 | A1 | 10/2004 | Whelan |
| 2004/0225358 | A1 | 11/2004 | Goble et al. |
| 2005/0065533 | A1 | 3/2005 | Magen et al. |
| 2005/0149187 | A1 | 7/2005 | Clark et al. |
| 2006/0149259 | A1 | 7/2006 | May et al. |
| 2006/0235516 | A1 | 10/2006 | Cavazzoni |
| 2006/0241657 | A1 | 10/2006 | Cerundolo |
| 2006/0265063 | A1 | 11/2006 | Goble et al. |
| 2007/0162123 | A1 | 7/2007 | Whittaker et al. |
| 2007/0208356 | A1 | 9/2007 | Cerundolo |
| 2007/0233151 | A1 | 10/2007 | Chudik |
| 2008/0058929 | A1 | 3/2008 | Whelan |
| 2008/0154271 | A1 | 6/2008 | Berberich et al. |
| 2009/0069846 | A1 | 3/2009 | Bull et al. |
| 2009/0099571 | A1 * | 4/2009 | Cresina ................ A61B 17/17 606/96 |
| 2009/0187244 | A1 | 7/2009 | Dross |
| 2010/0312341 | A1 | 12/2010 | Kaiser et al. |
| 2010/0324676 | A1 | 12/2010 | Albertorio et al. |
| 2011/0153018 | A1 | 6/2011 | Walters et al. |
| 2011/0282350 | A1 * | 11/2011 | Kowarsch ............ A61F 2/0805 606/96 |
| 2012/0095556 | A1 | 4/2012 | Re et al. |
| 2012/0197259 | A1 * | 8/2012 | Smith ................ A61B 17/1764 606/88 |
| 2013/0023988 | A1 | 1/2013 | Sinnott et al. |
| 2013/0090731 | A1 | 4/2013 | Walker |
| 2013/0096677 | A1 | 4/2013 | Myers et al. |
| 2015/0150616 | A1 | 6/2015 | Sharkey et al. |
| 2016/0089159 | A1 * | 3/2016 | Ardito ................ A61B 17/1714 606/96 |
| 2019/0008530 | A1 * | 1/2019 | Ardito ................ A61B 17/1714 |
| 2020/0375668 | A1 | 12/2020 | Pandya |
| 2021/0298919 | A1 * | 9/2021 | Lee ........... A61B 17/15 |
| 2022/0015778 | A1 * | 1/2022 | Ardito ................ A61B 17/1714 |
| 2023/0285016 | A1 * | 9/2023 | Lombardo ......... A61B 17/0401 606/232 |

\* cited by examiner

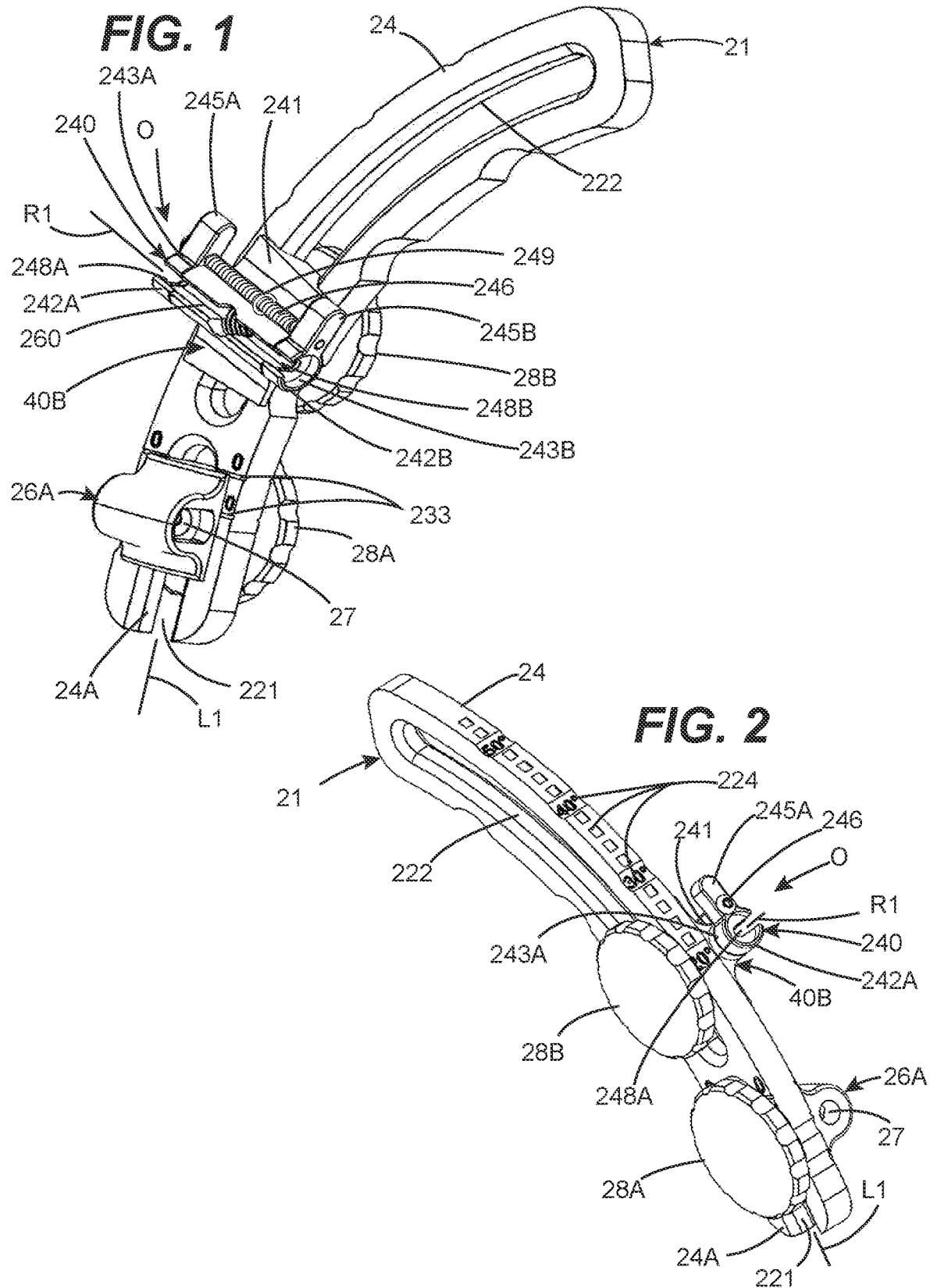

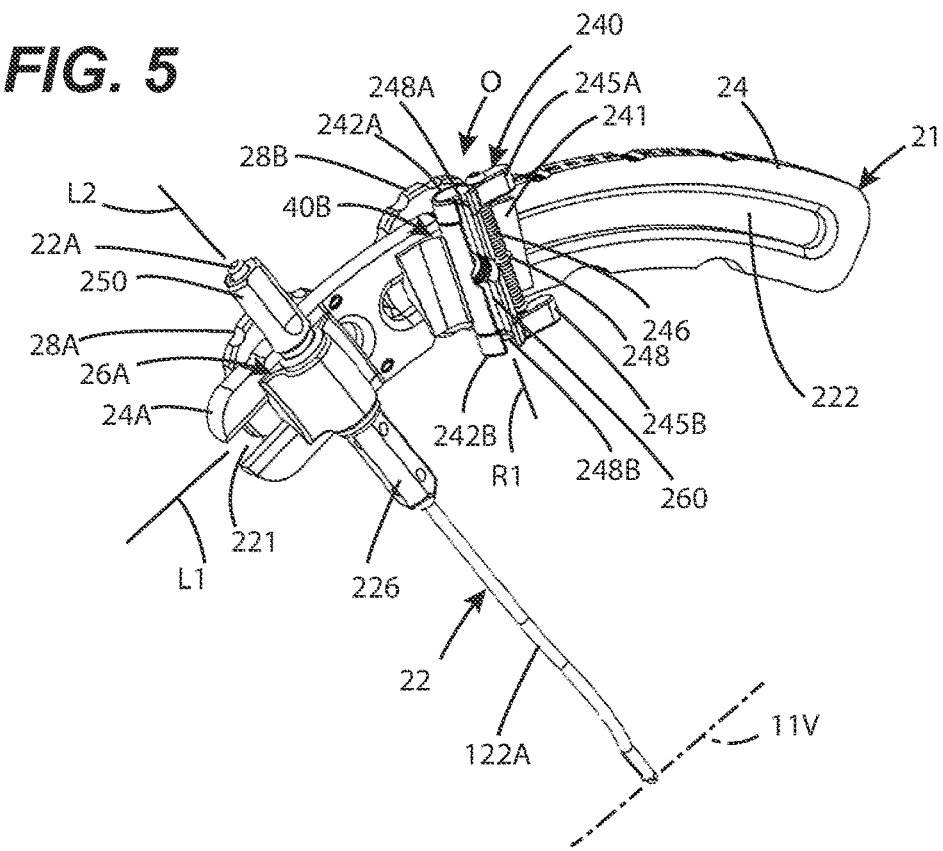
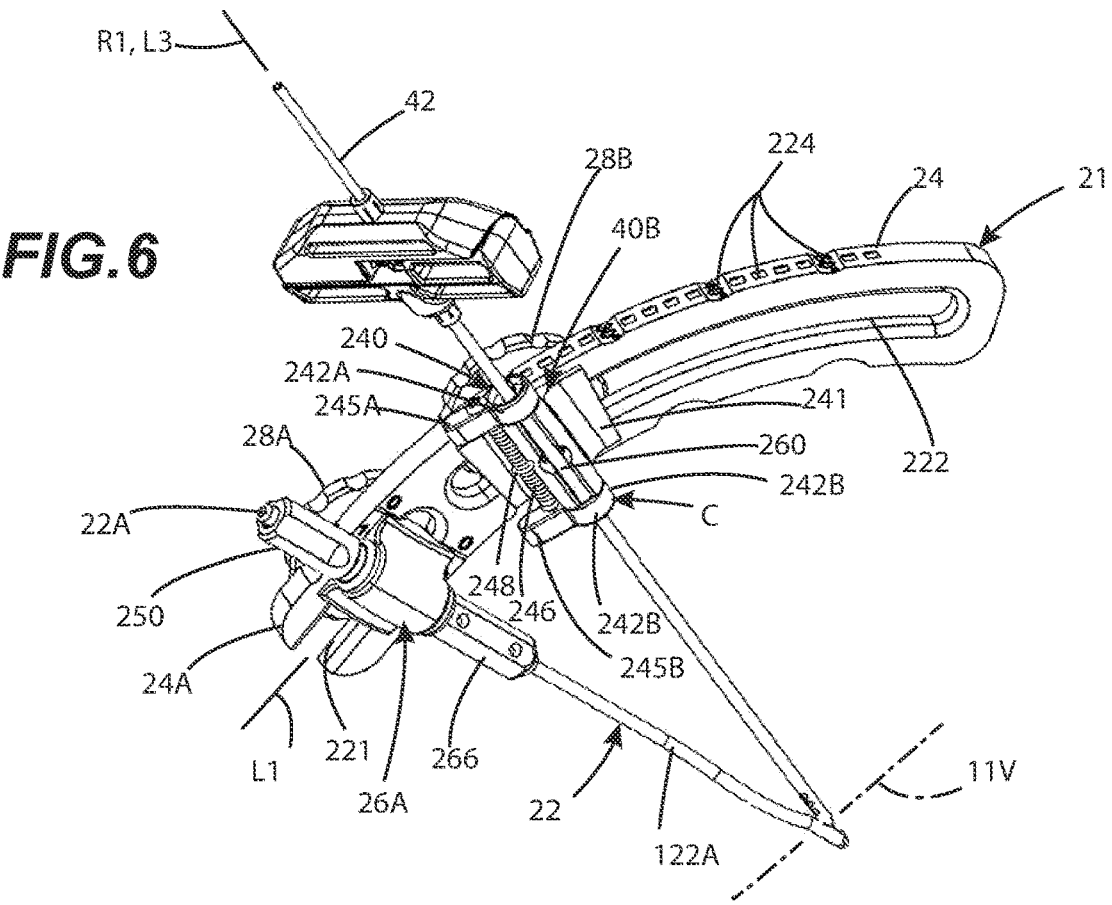

DEVICE ADAPTED FOR LATERAL ENGAGEMENT OF AN ELONGATED MEMBER

FIELD OF THE INVENTION

The present invention relates to devices adapted for lateral engagement of an elongated member with an attachment assembly thereof. More particularly, the present invention relates to surgical devices that are useful in the field of addressing lesions of bone marrow as well as other non-surgical procedures. Such surgical devices are particularly useful in enabling access to extra articular lesions or abnormalities or intra osseous lesions or bone marrow lesions in view of enabling a virtual path and access to an extra articular osseous lesion through intra articular localization.

BACKGROUND OF THE INVENTION

Surgical procedures to repair bone defects such as lesions or abnormalities typically involve scooping out the damaged tissue material. One such procedure is called curettage. In these procedures, the bone is removed or opened to provide access to the lesion or cancerous tumor. This effectively weakens the bone structure because not only has the damaged tissue been removed, but also some of the load bearing solid bone structure. This is particularly problematic in the spine, the knees and the shoulder and articulating joints.

Ideally the surgeon would prefer to attack the problematic tissue without damaging the surrounding load bearing bone tissue. This is particularly difficult, however, because the damaged tissue material to be removed is hidden behind the joint. The current state of the art does not allow for accessing as well as addressing lesions of bone distant to the entry point of the localizing site.

The presently available systems and techniques do not adequately address this concern. The present invention described below provides an improved device and associated technique for removing and/or treating the lesion, tumor or other abnormality without damaging the outer joint bone structure, and the surrounding cartilage, and soft tissue. This enables the healing and functionality of the repaired joint to be faster and far less painful.

Definitions

Bone cement: The bone cement PMMA (polymethylmethyacrylate) starts out as a liquid and hardens over time. It can be put into a hole in the bone in liquid form. As PMMA hardens, it gives off a lot of heat. The heat helps kill any remaining tumor cells. This allows PMMA to be used without cryosurgery for some types of bone tumors.

Bone Lesions: Various disorders can damage bones and result in bone lesions. Symptoms include bone pain or tenderness, and the injury can only be seen using special imaging tests. Bone lesions are abnormal areas of bone typically identified using an X-ray or MIll. Lucent bone lesions are caused by rapidly progressing bone injuries. Sclerotic lesions are bone injuries that develop more slowly, which allows the bone to attempt to wall off the damaged bone tissue. Bone lesions typically have cancerous and non-cancerous causes.

Bone Marrow Lesions: (BMLs), common osteoarthritis-related magnetic resonance imaging findings, are associated with osteoarthritis progression and pain.

Curettage: In this procedure, the doctor scoops out the tumor from the bone without removing a section of the bone. This leaves a hole in the bone. In some cases, after most of the tumor has been removed, the surgeon will treat the nearby bone tissue to kill any remaining tumor cells. This can be done with cryosurgery or by using bone cement.

Cryosurgery: For this treatment, liquid nitrogen is poured into the hole that is left in the bone after the tumor was removed. This extremely cold material kills tumor cells by freezing them. This treatment is also called cryotherapy. After cryosurgery, the hole in the bone can be filled by bone grafts or by bone cement.

Osteoarthritis: is the most common form of arthritis, affecting millions of people worldwide. It occurs when the protective cartilage on the ends of your bones wears down over time.

Osteochondritis dissecans: (OCD or OD) is a joint disorder in which cracks form in the articular cartilage and the underlying subchondral bone. OCD usually causes pain and swelling of the affected joint which catches and locks during movement. OCD is caused by blood deprivation in the subchondral bone. This loss of blood flow causes the subchondral bone to die in a process called avascular necrosis. The bone is then reabsorbed by the body, leaving the articular cartilage it supported prone to damage. The result is fragmentation (dissection) of both cartilage and bone, and the free movement of these bone and cartilage fragments within the joint space, causing pain and further damage. OCD can be difficult to diagnose because these symptoms are found with other diseases. However, the disease can be confirmed by X-rays, computed tomography (CT) or magnetic resonance imaging (MRI) scans.

Subchondral bone: bone located beneath or below the cartilage.

SUMMARY OF THE INVENTION

Disclosed herein are devices and associated techniques particularly useful for accessing extra articular lesions or abnormalities or intra osseous lesions or abnormalities or bone marrow lesions using intra articular localization has a guide, a locating arm, a set of attachment assemblies and a tubular sleeve. The guide component has a first portion and a second portion. The first portion has a first slotted opening extending a length from a first end. The second portion has an arcuate curvature extending from the first portion to a second end of the guide component with an elongated second arcuate slot in the second portion. The first attachment assembly is configured to be movably adjustable within the length of the first slotted opening. The second attachment assembly is configured to be movably adjustable along the elongated second arcuate slot. The locating arm has a first end and a second end. The second end is configured to be attached to the first attachment assembly. The locating arm has a localizing feature at the first end for defining a virtual pathway that extends perpendicularly to a centerline longitudinal axis of the locating arm. The tubular sleeve is configured to be attached to the second attachment feature. The tubular sleeve is for passing a pin or drill or punch along a selected path to form an entry access. The selected path extends toward the virtual pathway to form the entry access using intra articular localization.

The localizing feature at the first end of the locating arm may have any one of a plurality of configurations through which the virtual pathway extends. The first attachment assembly has a knob for tightening the first attachment assembly to the guide component (i.e., a main body). Similarly, the second attachment assembly has a knob for tightening the second attachment assembly to the guide component. Preferably, the first portion is straight and has a scale indicating a location of the first end of the locating arm. The guide component, at the first end, is configured at an open end of the slotted opening to pass onto the first attachment assembly along the length of the slotted opening and when the knob is tightened to set a vertical location of the virtual pathway at the first end of the locating arm relative to an axis of an implement engaged with the second attachment assembly. The locating arm has a shaft having a plurality of grooves. The grooves, when inserted into the first attachment assembly, engage a releasable detent. The detent enters one of the grooves to set an offset distance relative to the location of the virtual pathway and an axis of the drill or the pin or the punch.

In one or more embodiments, a surgical device comprises a device body and an attachment assembly mounted on the device body. The attachment assembly includes a main body and at least one closure body. The main body has an elongated recess therein. The elongated recess is configured for receiving an elongated member therein along an entire length thereof. The at least one closure body is rotatably mounted on the main body for enabling the elongated member to be positioned within the elongated recess via lateral movement when the at least one closure body is in a first rotational position relative to the main body and for inhibit the elongated member from being removed from within the elongated recess via lateral movement when the at least one closure body is moved away from the first rotational position toward a second rotational position relative to the main body.

In the one or more specific embodiments, the at least one closure body may be coupled to the main body for being rotated about a rotation axis extending one of parallel with and colinearly with a centerline longitudinal axis of the elongated recess.

In the one or more specific embodiments, the at least one closure body may have an access passage therein that is aligned with the elongated recess when in the first rotational position for enabling the elongated member to be positioned within the elongated recess and that becomes misaligned with the elongated recess when rotated to the second rotational position for retaining the elongated member within the elongated recess.

In the one or more specific embodiments, a closed bottom end of the elongated recess and an open upper end of the elongated recess may be respectively aligned with a closed bottom end of the access passage and an open upper end of the access passage when the at least one closure body is in the first rotational position.

In the one or more specific embodiments, the access passage of the at least one closure body and the elongated recess may each be generally U-shaped.

In the one or more specific embodiments, the at least one closure body may include two closure bodies each independently mounted on the main body for being rotated about a rotation axis with the elongated recess extending between the two closure bodies.

In the one or more specific embodiments, the two closure bodies may be coupled to each other to inhibit relative rotational movement therebetween.

In the one or more specific embodiments, the rotation axis may extend one of parallel and colinearly with a centerline longitudinal axis of the elongated recess.

BRIEF DESCRIPTION OF THE DRAWINGS

The invention will be described by way of example and with reference to the accompanying drawings in which:

FIG. 1 is a first perspective view of a guide system device in accordance with an embodiment of the disclosures made herein.

FIG. 2 is a second perspective view of the guide system device of FIG. 1.

FIG. 5 is a perspective view of the guide system device of FIG. 1 having a guide member engaged therewith and a retention assembly of a second attachment assembly thereof in an open configuration.

FIG. 6 is an exploded view of the guide system device of FIG. 1 having a guide member and tubular sleeve engaged therewith and a retention assembly of a second attachment assembly thereof in a closed configuration.

DETAILED DESCRIPTION OF THE INVENTION

Figure 3:
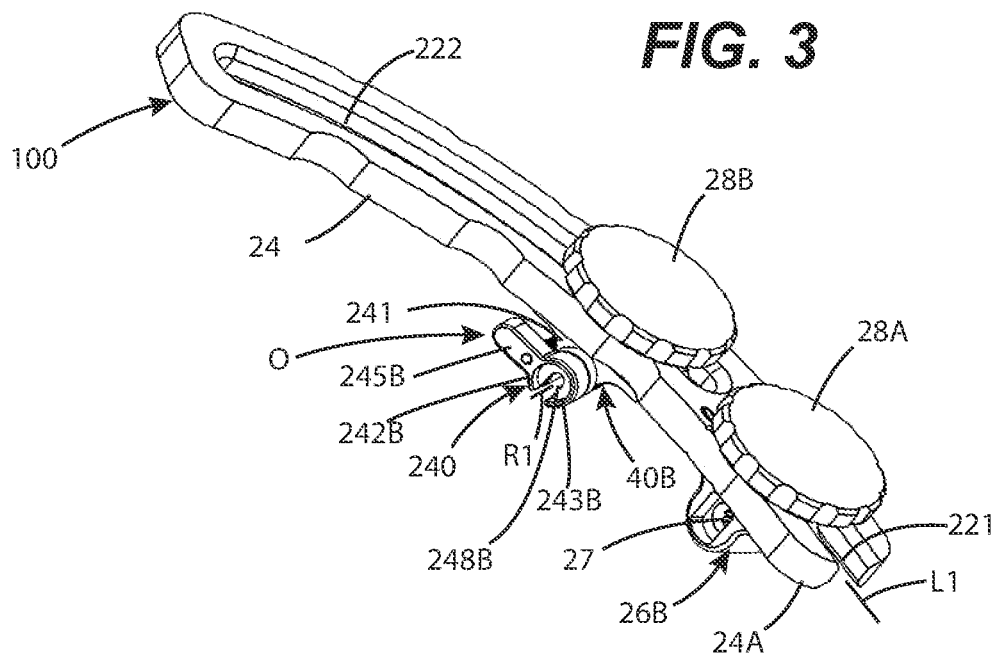
FIG. 3 is a third perspective view of the guide system device of FIG. 1.

Referring to FIGS. 1-8, a guide component 21 of a guide assembly device (device) in accordance with an embodiment of the disclosures made herein has a first portion 24A with a first slotted opening 221 for receiving a first attachment assembly 26A. The first slotted opening 221 is generally straight whereby a longitudinal axis of the first slotted opening 221 extends colinearly with a longitudinal reference axis L1. The first attachment assembly 26A is configured to receive a locating arm 22, as best shown in FIGS. 5 and 6. The locating arm 22 has a first end 22A and a second end 22B opposite the first end 22A. The first end 22A of the locating arm 22 is fixedly engaged with the first attachment assembly 26A by suitable means. For example, as shown, the first end 22A of the locating arm 22 extends through an opening 27 of the first attachment assembly 26A and an engagement member 226 of the locating arm 22 engages a mating surface of the first attachment assembly 26A. A centerline longitudinal axis L2 of the locating arm 22 extends colinearly with a centerline longitudinal axis of the opening 27 of the first attachment assembly 26A. An arm retention body 227 engages the first end 22A of the locating arm 22 (e.g., by a mating threaded interface) for securing the first end 22A of the locating arm 22 in a fixed position with respect to the first attachment assembly 26A. The arm retention body 227 may be adapted for enabling axial adjustment of the locating arm 22 with respect to the first attachment assembly 26A (e.g., the engagement member 226 being movably engaged with an elongated member 122A of the locating arm 22 for enabling selective placement of the elongated member 122A relative to the engagement member 226).

A tip portion of the second end 22B of the locating arm 22 includes a virtual pathway alignment feature which may be a pin having the virtual axis extending through a tip of thereof along a longitudinal centerline axis thereof, a disk-shaped end with an aperture therein or the like. As previously disclosed, a center of the virtual pathway alignment feature (e.g., aperture 32) defines a virtual pathway 11V, in that the virtual pathway 11V is a perpendicular line passing through the aperture 32 center vertically relative to the locating arm 22. A localizing pin 30 may be press fit or securely fixed in the aperture 32 whereby the pin 30 may penetrate the tissue to help insure the second end 22B does not move during manipulation of the guide component 21.

The first attachment assembly 26A has a knob 28A (i.e., securing body) for securing a main body 28 of the first attachment assembly 26A in selected position along a length of the first slotted opening 221. To this end, the knob 28A may be in threaded engagement with the main body 28. For example, the knob 28A may include a threaded stud that passes through the first slotted opening 221 and into engagement with a mating threaded passage within the main body 28 of the first attachment assembly 26A. In view of the disclosures made herein, a skilled person will appreciate other various forms of securement arrangements for securing the main body 28 of the first attachment assembly 26A in a selected position along a length of the first slotted opening 221.

As shown in FIGS. 1-7, the guide component 21 has a second portion 24 that is arcuately curved. The second portion 24 has a second slotted opening 222 therein. A second attachment assembly 40B is engaged with the second portion 24 visa the second slotted opening 222. Such engagement permits movement of the second attachment assembly 40B along a length of the second slotted opening 222. The second attachment assembly 40B may be secured in a desired position along the length of the second slotted opening 222 for enabling the second attachment assembly 40B to be set at a position corresponding to a desired entry access location of an instrument such as a drill relative to the virtual pathway 11V, as will be discussed. The second slotted opening 222 preferably has a constant radius of curvature such that when the second attachment assembly 40A is secured in the fixed position relative to the guide 21, a tubular sleeve 42 (or other elongated body) can be inserted into the second attachment assembly 40A. As shown, the second slotted opening 222 of the second portion 24 has a closed end, but this end could alternatively be open and vice versa for the first slotted opening 221 of the first end 24A. The tubular sleeve 42 may have a manipulation body 42A engaged therewith for enabling the tubular sleeve 42 to be positioned and rotated relative a subject structure of a patient.

Figure 4:
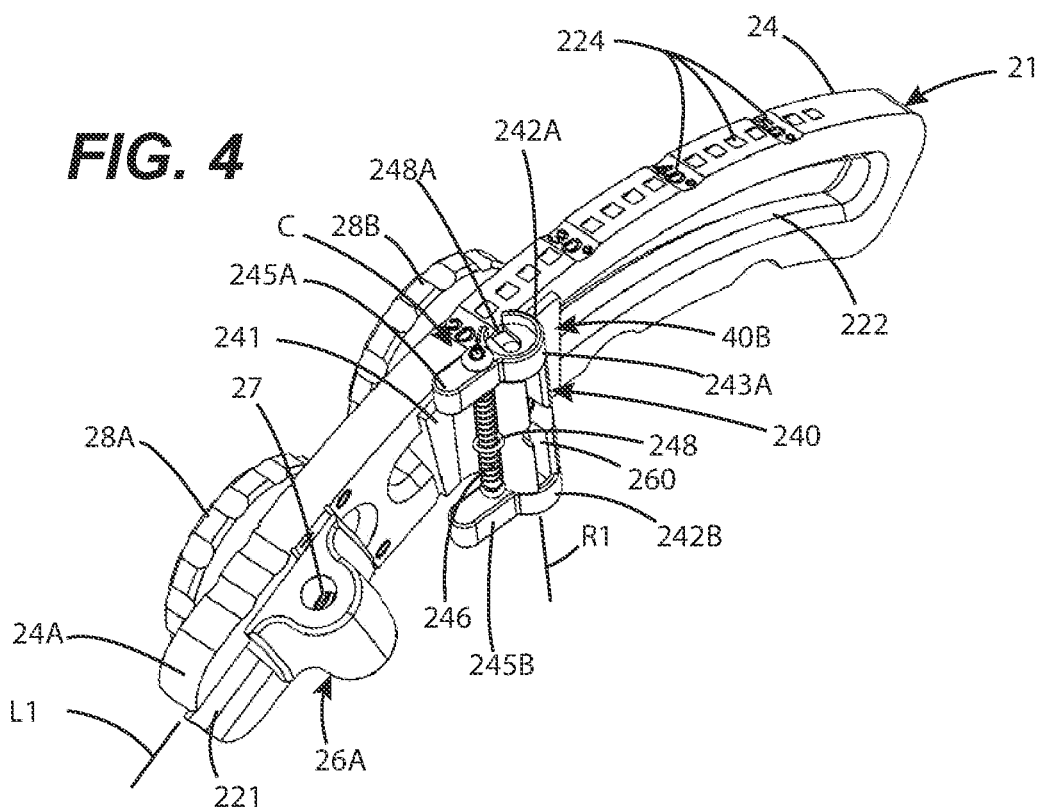
FIG. 4 is a fourth perspective view of the guide system device of FIG. 1.
Figure 7:
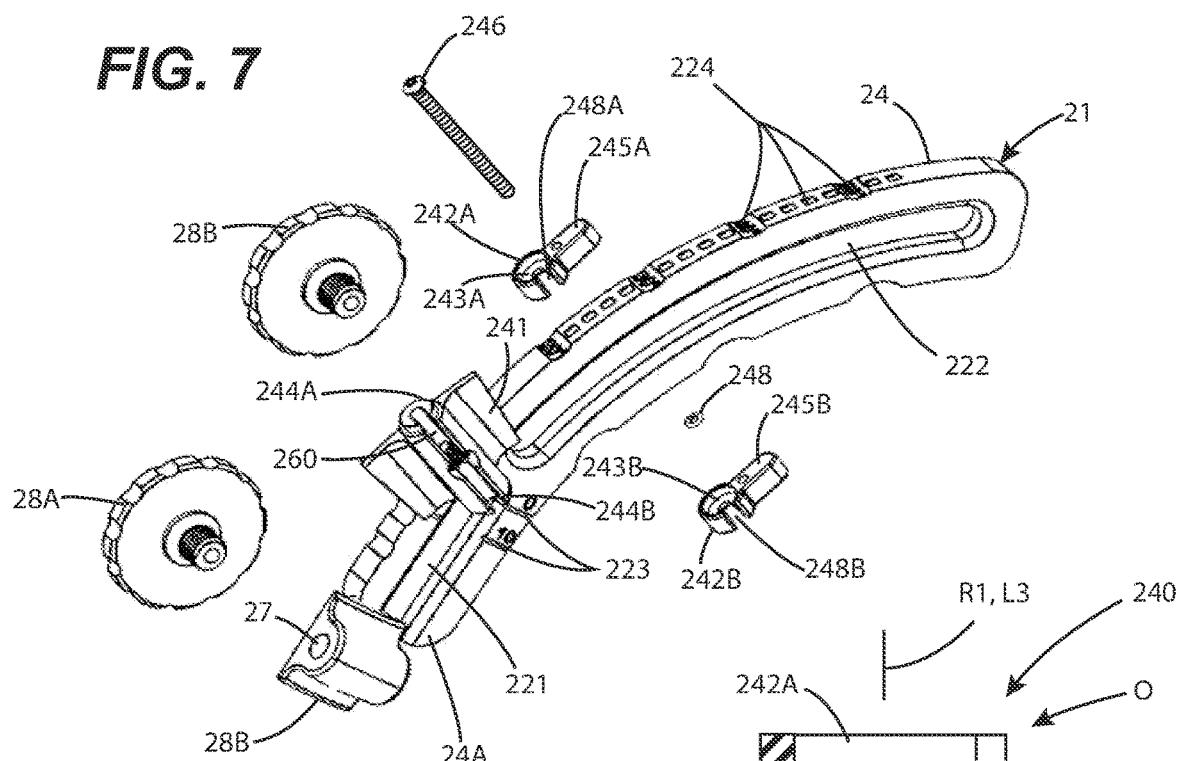
FIG. 7 is an exploded view of the guide system device of FIG. 1.
Figure 8:
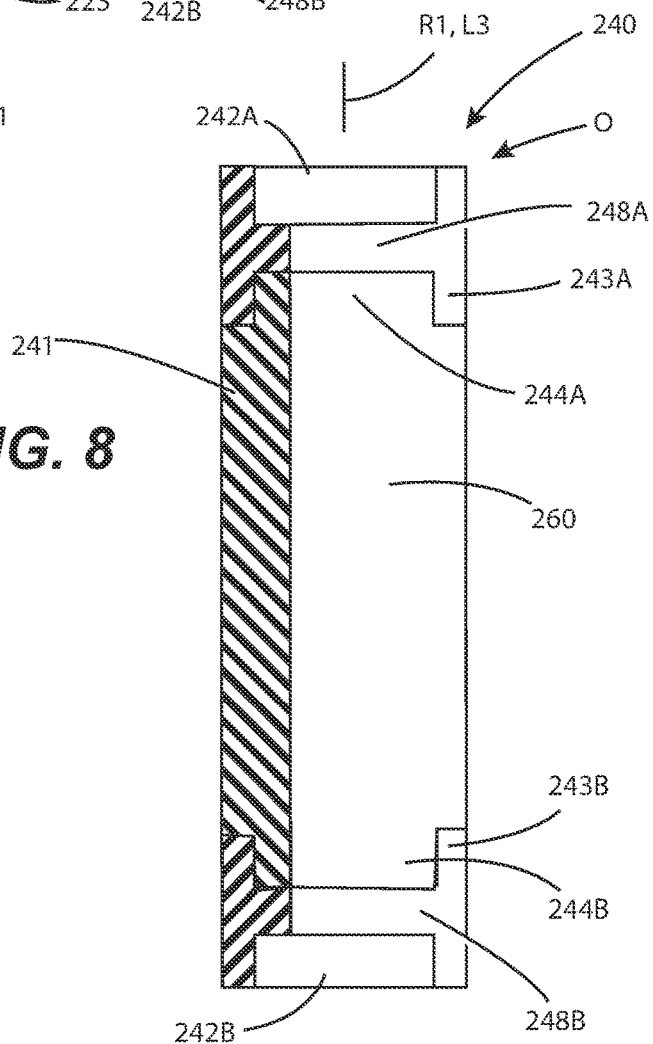
FIG. 8 is a cross-sectional view of a retention assembly of a second attachment assembly of the guide system device of FIG. 1.

As best shown in FIGS. 1 and 7, the first slotted opening 221 has graduations 223 associated therewith that identify a location of the first attachment assembly 26A relative to the guide component 21. Each gradation 223 preferably has reference location indicia associated therewith. In use, the first attachment assembly 26A can be shifted upward or downward in the first slotted opening 221 to any desired location at the discretion of the surgeon (e.g., for virtual pathway offset location) and a desired position can be noted based upon location of the first attachment assembly 26A relative to the graduations 223 and/or associated reference location indicia. Similarly, as best shown in FIGS. 32, 4 and 7, the second slotted opening 222 has a plurality of graduations 224 associated therewith that identify a location of the second attachment assembly 40A relative to the guide component 21. Each gradation 224 preferably has reference location indicia associated therewith. In use, the second attachment assembly 40A can be shifted along the second slotted opening 222 to any desired location at the discretion of the surgeon (e.g., angle for the entry access relative to the virtual pathway) and a desired position can be noted based upon location of the second attachment assembly 40A relative to the graduations 224 and/or associated reference location indicia.

The second attachment assembly 40A has a knob 28B (i.e., securing body) for securing a main body 241 of the second attachment assembly 26A in selected position along a length of the second slotted opening 222. To this end, the knob 28B may be in threaded engagement with the main body 28. For example, the knob 28A may include a threaded stud that passes through the second slotted opening 222 and into engagement with a mating threaded passage within the main body 241 of the second attachment assembly 40A. In view of the disclosures made herein, a skilled person will appreciate other various forms of securement arrangements for securing the main body 241 of the second attachment assembly 40A in a selected position along a length of the second slotted opening 222.

The second attachment assembly 40A includes a retention assembly 240. The retention assembly 240 provides for selective retention and release of a tubular sleeve 42 engaged within an elongated recess 260 of the second attachment assembly 40A. As shown in FIG. 6, a centerline longitudinal axis of a central passage of the tubular sleeve 42 extends colinearly with a longitudinal reference axis L3 of the elongated recess 260. The retention assembly 240 permits rotation and axial translation of the tubular sleeve 42 relative to the second attachment assembly 40A during such retention of the tubular sleeve 42. Such rotation and axial translation may be manually provided or provided via a powered rotary tool such as, for example, a drill.

As shown in FIG. 5-8, the retention assembly 240 includes spaced-apart closure bodies 242A, 242B that each have a mounting portion 243A, 243B that is rotatably engaged with a respective mating extension portion 244A, 244B of the main body 241 of the second attachment assembly 40A. Preferably, the closure bodies 242A, 242B are coupled to each other to enable synchronous rotate about a rotational axis R1 when a rotational movement force is applied to a control portion 245A, 245B of either one of the closure bodies 242A, 242B. The rotational axis R1 preferably extends one of parallel with and colinearly with a centerline longitudinal axis of the elongated recess 260.

Such coupling may be provided by a coupling member 246 (e.g., a threaded fastener) that is fixedly engaged with both closure bodies 242A, 242B for limiting and preferably inhibiting relative movement between the closure bodies 242A, 242B. The retention assembly 240 may further include an anti-rotation element 249 that limits unintentional rotation of the closure bodies 242A, 242B about the rotational axis R1. For example, the coupling member 246 may be a threaded fastener having an O-ring mounted thereon and engaged (e.g., compressedly) with an exterior surface of the main body 241 of the second attachment assembly 40A whereby friction between the O-ring and the exterior surface of the main body 241 provides friction that limits such unintentional rotation of the closure bodies 242A, 242B about the rotational axis R1.

When the retention assembly 240 is in an open configuration O, each of the access passages 248A, 248B is aligned (i.e., suitably aligned or fully aligned) with the elongated recess 260 (e.g., a slot) in the main body 241 of the second attachment assembly 40A, as best shown in FIG. 3. In this aligned configuration, the tubular sleeve 42 (or other elongated body) may be positioned within and removed from within the elongated recess 260 via lateral movement relative to the elongated recess 260 of the second attachment assembly 40A. For example, the device may be moved in a lateral motion for causing the tubular sleeve 42 to become positioned within or removed from within the elongated recess 260. Through rotation of the retention assembly 240, each of the access passages 248A, 248B becomes misaligned with the elongated recess 260 (e.g., a slot), as best shown in FIG. 4, whereby the retention assembly 240 is in a closed configuration C. In the closed configuration C, as best shown in FIG. 6, the closure bodies 242A, 242B inhibit the tubular sleeve 42 from being removed from within the elongated recess 260 via lateral movement (i.e., retain the tubular sleeve 42 within the elongated recess 260) while still permitting axial movement and rotation of the tubular sleeve 42 relative to the main body 241 of the second attachment assembly 40A.

Each of the closure bodies 242A, 242B of the retention assembly 240 has an access passage 248A, 248B. As shown, the access passage 248A, 248B and the elongated recess 260 may each be generally U-shaped—i.e., have a closed bottom end and an open upper end, as best shown in FIGS. 2, 3, 4 and 7. The closed bottom end of the elongated recess and the open upper end of the elongated recess are respectively aligned with the closed bottom end of the access passage and the open upper end of the access passage when the closure bodies are in the first rotational position. An end-view profile of the elongated recess 260 (i.e., as viewed along the rotational axis R1) and a plan view profile (i.e., as viewed along the rotational axis R1) of the access passages 248A, 248B may be identical. Alternatively, the plan view profile of the access passages 248A, 248B may encompass the end-view profile of the elongated recess 260. The plan view profile of the access passages 248A, 248B is suitably shaped for allowing the tubular sleeve (or other elongated member) to be placed in to the elongated recess 260 via lateral movement when the retention assembly 240 is in the open configuration O.

In view of the disclosures made herein, a skilled person will appreciate that the closure bodies 242A, 242B located at the opposing ends of the main body 241 of the second attachment assembly 40A can be replaced by one or more one closure bodies located inboard of the opposing ends of the main body 241. For example, a single closure body may be rotatably mounted on the main body 241 at or near a mid-point thereof for enabling an elongated member (e.g., the tubular sleeve 42) to be side loaded into the elongated recess 260 of the second attachment assembly 40A with the single closure body in an open configuration and then the single closure body may be moved to a closed orientation (e.g., rotated) for securing the elongated member within the elongated recess 260 of the second attachment assembly 40A. In preferred embodiments, a length of the single closure body and the length of the elongated recess 260 are jointly configured to limit off-axis skewing of a centerline longitudinal axis of the elongated member relative to the longitudinal reference axis L3 of the elongated recess 260.

Devices in accordance with embodiments of the disclosures made herein can be used in procedure such as the surgical procedures discussed above. Beneficially, such devices can be utilized in the surgical procedures in a manner that beneficially utilize a virtual pathway and intersecting access pathway provided for by such devices. The ability to laterally position an elongated body (e.g., a tubular sleeve, drill, rod shaped body or the like) within an elongated recess (e.g., a slot) of an attachment assembly of a device and remove it therefrom via lateral movement is advantageous in regard to efficiency and effectiveness of procedures that require the device to be selectively engaged with and/or disengaged from the device during the procedure. For example, in the aforementioned surgical procedures for repairing bony structures exhibiting a lesion or other abnormality, it can be useful to engage the elongated body with the attachment assembly of the device or disengage the elongated body therefrom before or after placement of the elongated body relative to an anatomical (e.g., bony) structure of a patient.

A fixture material such as a cement (e.g., bone cement such as PMMA) can be deposited into a cavity through the tube or sleeve 42 for treating or fixing an ailment associated with the cavity. In this regard, devices in accordance with the disclosures made herein may be used in addressing lesions of bone which may or may not be visualized arthroscopically. This could be in situations where the patient has intact articular cartilage, such as the situation with osteochondritis dissecans. The surgeon can tell where the lesion is by probing. There can be situations dealing with osteoarthritis or other lesions of the bone marrow where the subchondral bone is intact. In either case, the surgeon wants to be able to locate where the lesion of the bone is that can't be visualized, it is essentially extra articular, it is within the bone. This could be termed a bone marrow lesion (BML), but in this technique, the surgeon uses intra articular techniques to access the lesion.

In accordance with embodiments of the disclosures made herein, it is highly beneficial to have the capability to first place a tip portion of the elongated body at (e.g., on or within) a desired location of the bony structure, to then securely engage (i.e., side load) the elongated body with the attachment assembly and to then use the device to angularly position the elongated body relative to the bony structure. Such side loading provides for a simplified means of engaging the elongated body with the device in comparison to devices that required engagement over an exposed end portion of the elongated body. Such advantageous operability arises from the capability of sideloading (i.e., lateral engagement) and associated lateral disengagement of an elongated tubular member (e.g., a trocar) fixed in bone vis-a-vis only end loading/disengagement and, in turn, provides for precision of entry point location and target point access, where such entry point location and target point access are each independent of a preset guide device.

Devices in accordance with embodiment of the disclosures made herein provide for precise localization of a lesion or other defect and a way to access it while minimizing load bearing bone structure damage caused by the surgical repair by essentially leveraging the inventor's angled osteal tunnel concept of creating blind tunnels. One example where this technique of use of a device in accordance with embodiments of the present invention is most useful is to access the lesion or other defect from within a knee joint—i.e., intra-articular. A surgeon can position a tip portion of a locating arm of the device from within the knee joint onto or into the bone even going through intact cartilage it necessary. Then, from coming outside of the joint with a drill (or other elongated body), the surgeon can then articulate to a blind spot or point within bone at the location within the lesion or other defect knowing that it is accurate based on the precision of the device i.e., at a point of intersection of the centerline longitudinal axis of the drill and the virtual axis defined by the tip portion of the locating arm. This technique uniquely allows for blind targeting a point or location within bone.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A surgical device, comprising:
a device body; and
an attachment assembly mounted on the device body, wherein the attachment assembly includes a main body and at least one closure body, wherein the main body has an elongated recess therein, wherein the elongated recess is configured for receiving an elongated member therein along an entire length thereof, wherein the at least one closure body is rotatably mounted on the main body for enabling the elongated member to be positioned within the elongated recess via lateral movement when the at least one closure body is in a first rotational position relative to the main body and for inhibiting the elongated member from being removed from within the elongated recess via lateral movement when the at least one closure body is moved away from the first rotational position toward a second rotational position relative to the main body, wherein the at least one closure body is coupled to the main body for being rotated about a rotation axis extending collinearly with a centerline longitudinal axis of the elongated recess,
wherein the at least one closure body includes two closure bodies each independently mounted on the main body for being rotated about the rotation axis, and
wherein the elongated recess extends between the two closure bodies.

2. The surgical device of claim 1 wherein at least one closure body has an access passage therein that is aligned with the elongated recess when in the first rotational position for enabling the elongated member to be positioned within the elongated recess and that becomes misaligned with the elongated recess when rotated to the second rotational position for retaining the elongated member within the elongated recess.

3. The surgical device of claim 2, wherein the elongated recess and the access passage of at least one closure body each comprise a closed bottom end and an open upper end and wherein the closed bottom end of the elongated recess and the open upper end of the elongated recess are respectively aligned with the closed bottom end of the access passage and the open upper end of the access passage when the at least one closure body is in the first rotational position.

4. The surgical device of claim 2 wherein the access passage of at least one closure body and the elongated recess are each generally U-shaped.

5. The surgical device of claim 1 wherein the two closure bodies are coupled to each other to inhibit relative rotational movement therebetween.

6. The surgical device of claim 5 wherein each of the closure bodies has an access passage therein that is aligned with the elongated recess when in the first rotational position for enabling the elongated member to be positioned within the elongated recess and that becomes misaligned with the elongated recess when rotated to the second rotational position for retaining the elongated member within the elongated recess.

7. The surgical device of claim 6 wherein a plan view profile of the access passage of at least one closure body is one of identical to or encompassing of an end-view profile of the elongated recess when the at least one closure body is in the first rotational position.

8. The surgical device of claim 1 wherein each of the closure bodies has an access passage therein that is aligned with the elongated recess when in the first rotational position for enabling the elongated member to be positioned within the elongated recess and that becomes misaligned with the elongated recess when rotated to the second rotational position for retaining the elongated member within the elongated recess.

9. The surgical device of claim 8 wherein the access passages and the elongated recess each comprise a closed bottom end and an open upper end, and wherein the closed bottom end of the elongated recess and the open upper end of the elongated recess are respectively aligned with the closed bottom end of the access passage and the open upper end of the access passage of each of the closure bodies when the closure bodies are in the first rotational position.

10. A surgical device, comprising:
a guide component having a first portion including a first slotted opening that is generally straight and a second portion including a second slotted opening that is arcuate;
a first attachment assembly engaged with the first slotted opening, wherein the first attachment assembly is selectively positionable along a length of the first slotted opening; and
a second attachment assembly engaged with the second slotted opening, wherein the second attachment assembly is selectively positionable along a length of the second slotted opening, wherein the second attachment assembly includes a main body having an elongated recess therein, wherein the elongated recess is configured for receiving a tubular sleeve therein along an entire length thereof, wherein the second attachment assembly includes spaced-apart closure bodies rotatably mounted on the main body, wherein the elongated recess extends between the spaced-apart closure bodies, wherein each of the closure bodies comprises an access passage, wherein the access passage of each of the closure bodies and the elongated recess are in sufficient alignment for enabling the tubular sleeve to be positioned within the elongated recess when the closure bodies are in a first rotational position, and wherein the access passage of each of the closure bodies and the elongated recess are in sufficient misalignment for enabling the closure bodies to retain the tubular sleeve within the elongated recess when the closure bodies are each moved to a second rotational position.

11. The surgical device of claim 10 wherein the two closure bodies are coupled to each other to inhibit relative rotational movement therebetween.

12. The surgical device of claim 11 wherein the closure bodies comprise a rotation axis and the rotation axis extends one of parallel and collinearly with a centerline longitudinal axis of the elongated recess.

13. The surgical device of claim 12 wherein the elongated recess and the access passages each comprise a closed bottom end and an open upper end, and wherein the closed bottom end of the elongated recess and the open upper end of the elongated recess are respectively aligned with the closed bottom end of the access passage and the open upper end of the access passage of each of the closure bodies when the closure bodies are in the first rotational position.

14. The surgical device of claim 10 wherein the elongated recess and the access passages each comprise a closed bottom end and an open upper end, and wherein the closed bottom end of the elongated recess and the open upper end of the elongated recess are respectively aligned with the closed bottom end of the access passage and the open upper end of the access passage of each of the closure bodies when the closure bodies are in the first rotational position.

15. The surgical device of claim 10 wherein a plan view profile of the access passages of each of the closure bodies is one of identical to or encompassing of an end-view profile of the elongated recess when the closure bodies are in the first rotational position.

\* \* \* \* \*